US010193133B2

(12) United States Patent
Cho et al.

(10) Patent No.: US 10,193,133 B2
(45) Date of Patent: Jan. 29, 2019

(54) METHOD FOR MANUFACTURING OF METAL OXIDE NANOPARTICLES AND METAL OXIDE NANOPARTICLES THEREBY

(71) Applicant: KOREA ADVANCED INSTITUTE OF SCIENCE AND TECHNOLOGY, Daejeon (KR)

(72) Inventors: Sung Oh Cho, Daejeon (KR); Ali Ghafar, Daejeon (KR); Yang Jeong Park, Gyeonggi-do (KR)

(73) Assignee: KOREA ADVANCED INSTITUTE OF SCIENCE AND TECHNLOGY, Daejeon (KR)

( * ) Notice: Subject to any disclaimer, the term of this patent is extended or adjusted under 35 U.S.C. 154(b) by 224 days.

(21) Appl. No.: 14/685,864

(22) Filed: Apr. 14, 2015

(65) Prior Publication Data
US 2015/0303449 A1    Oct. 22, 2015

(30) Foreign Application Priority Data

Apr. 17, 2014  (KR) .................. 10-2014-0045884

(51) Int. Cl.
*H01M 4/131*     (2010.01)
*H01M 10/0525*   (2010.01)
(Continued)

(52) U.S. Cl.
CPC ............ *H01M 4/131* (2013.01); *B01J 21/04* (2013.01); *B01J 21/063* (2013.01); *B01J 21/066* (2013.01);
(Continued)

(58) Field of Classification Search
None
See application file for complete search history.

(56) References Cited

U.S. PATENT DOCUMENTS 6,676,821 B1    1/2004 Hempelmann et al.
2008/0279760 A1* 11/2008 Torardi ................. B82Y 30/00
                                                 423/612
(Continued)

FOREIGN PATENT DOCUMENTS

JP    2002524661 A    8/2002
JP    2013538289 A    10/2013
(Continued)

OTHER PUBLICATIONS

English Abstract for Korean Publication No. 10-2004-0048093, published Jun. 7, 2004, 1 pg.
(Continued)

*Primary Examiner* — Wyatt P McConnell
(74) *Attorney, Agent, or Firm* — Fredrikson & Byron, P.A.

(57) ABSTRACT

The present invention relates to a method for preparing metal oxide nanoparticles and metal oxide nanoparticles prepared thereby. The method includes: dipping a cathode and an anode formed of a metal for forming oxide, in an inorganic electrolyte solution containing halogen salt, and applying voltage to the anode and the cathode to form, on the anode, metal oxide forming an anode surface. According to a method of the present invention, disadvantages of typical nanoparticle synthesizing methods may be solved to cheaply and rapidly manufacture nanoparticles having various structures through a single process without using a surfactant. In practicing a method of the invention, metal oxide nanoparticles may be rapidly formed, nanoparticles having excellent crystallinity may be produced, and factors of the anodizing method, such as voltage, temperature, an electrolyte, and an electrolyte concentration may be changed to simply adjust a shape of the nanoparticles.

12 Claims, 17 Drawing Sheets

(51) Int. Cl.
| | | |
|---|---|---|
| H01M 4/485 | (2010.01) | |
| C01G 15/00 | (2006.01) | |
| C01G 19/02 | (2006.01) | |
| C01G 9/02 | (2006.01) | |
| C01G 25/02 | (2006.01) | |
| C01F 7/02 | (2006.01) | |
| C01G 23/047 | (2006.01) | |
| C01G 53/04 | (2006.01) | |
| C01G 49/06 | (2006.01) | |
| C01G 3/02 | (2006.01) | |
| C01G 53/00 | (2006.01) | |
| B01J 23/08 | (2006.01) | |
| B01J 23/14 | (2006.01) | |
| B01J 23/06 | (2006.01) | |
| B01J 21/06 | (2006.01) | |
| B01J 21/04 | (2006.01) | |
| B01J 23/755 | (2006.01) | |
| B01J 23/745 | (2006.01) | |
| B01J 23/72 | (2006.01) | |
| B01J 23/75 | (2006.01) | |
| C01G 51/00 | (2006.01) | |
| C25B 1/00 | (2006.01) | |
| C25D 11/08 | (2006.01) | |
| C25D 11/16 | (2006.01) | |
| C25D 11/26 | (2006.01) | |
| C25D 11/34 | (2006.01) | |
| C01F 7/42 | (2006.01) | |
| B01J 37/03 | (2006.01) | |
| B01J 37/34 | (2006.01) | |
| B01J 23/74 | (2006.01) | |
| B01J 35/00 | (2006.01) | |
| B01J 35/02 | (2006.01) | |
| A61K 9/51 | (2006.01) | |

(52) U.S. Cl.
CPC ............. *B01J 23/06* (2013.01); *B01J 23/08* (2013.01); *B01J 23/14* (2013.01); *B01J 23/72* (2013.01); *B01J 23/74* (2013.01); *B01J 23/745* (2013.01); *B01J 23/75* (2013.01); *B01J 23/755* (2013.01); *B01J 35/002* (2013.01); *B01J 35/0013* (2013.01); *B01J 35/023* (2013.01); *B01J 37/031* (2013.01); *B01J 37/348* (2013.01); *C01F 7/02* (2013.01); *C01F 7/428* (2013.01); *C01G 3/02* (2013.01); *C01G 9/02* (2013.01); *C01G 15/00* (2013.01); *C01G 19/02* (2013.01); *C01G 23/047* (2013.01); *C01G 25/02* (2013.01); *C01G 49/06* (2013.01); *C01G 51/00* (2013.01); *C01G 51/006* (2013.01); *C01G 53/00* (2013.01); *C01G 53/04* (2013.01); *C25B 1/00* (2013.01); *C25D 11/08* (2013.01); *C25D 11/16* (2013.01); *C25D 11/26* (2013.01); *C25D 11/34* (2013.01); *H01M 4/485* (2013.01); *H01M 10/0525* (2013.01); *A61K 9/5115* (2013.01); *C01P 2002/72* (2013.01); *C01P 2002/85* (2013.01); *C01P 2004/02* (2013.01); *C01P 2004/03* (2013.01); *C01P 2004/04* (2013.01); *C01P 2004/51* (2013.01); *C01P 2004/64* (2013.01)

(56) References Cited

U.S. PATENT DOCUMENTS

| | | | | |
|---|---|---|---|---|
| 2010/0258759 | A1* | 10/2010 | Archer | B82Y 30/00 252/62.56 |
| 2011/0303552 | A1* | 12/2011 | Hyam | B82Y 30/00 205/538 |
| 2012/0074398 | A1* | 3/2012 | Fujita | H01L 51/5225 257/40 |
| 2013/0052533 | A1* | 2/2013 | Chun | H01M 4/483 429/218.1 |
| 2013/0095140 | A1* | 4/2013 | Baron | A61K 9/2054 424/400 |
| 2013/0199673 | A1* | 8/2013 | Yanson | B01J 23/462 148/24 |
| 2013/0302668 | A1* | 11/2013 | Lim | H01M 10/056 429/200 |
| 2013/0334097 | A1* | 12/2013 | Patino | B01J 21/04 208/14 |

FOREIGN PATENT DOCUMENTS

| KR | 1020040048093 A | 6/2004 |
|---|---|---|
| KR | 20120051178 A | 5/2012 |

OTHER PUBLICATIONS

English abstract for Japanese Publication No. 2002-524661, Aug. 6, 2002.
English abstract for Japanese Publication No. 2013-538289, Oct. 10, 2013, 1 page.
English abstract for Korean Publication No. 2012-0051178, May 22, 2012, 2 pages.

* cited by examiner

[Fig. 1]
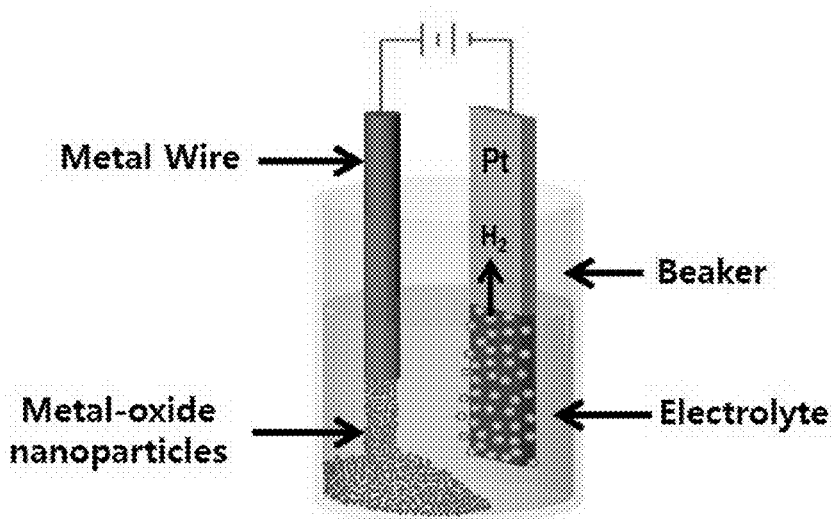
[Fig. 2]
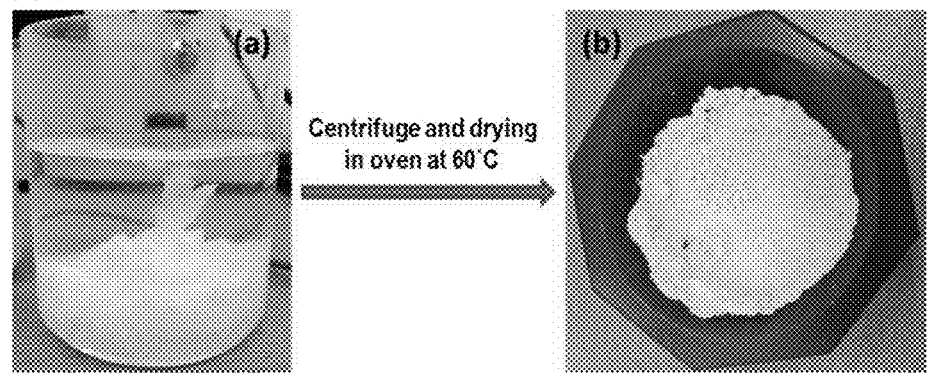

[Fig. 3]
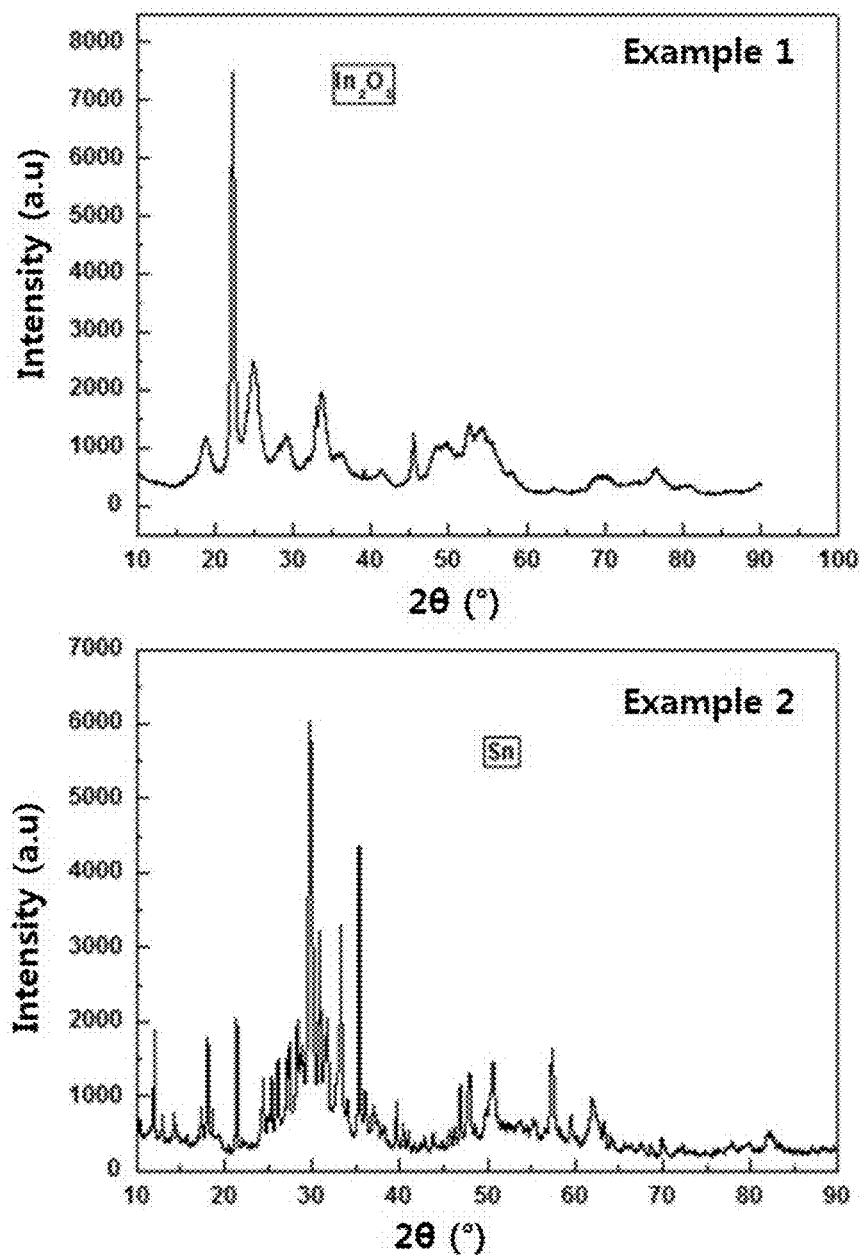

[Fig. 4]
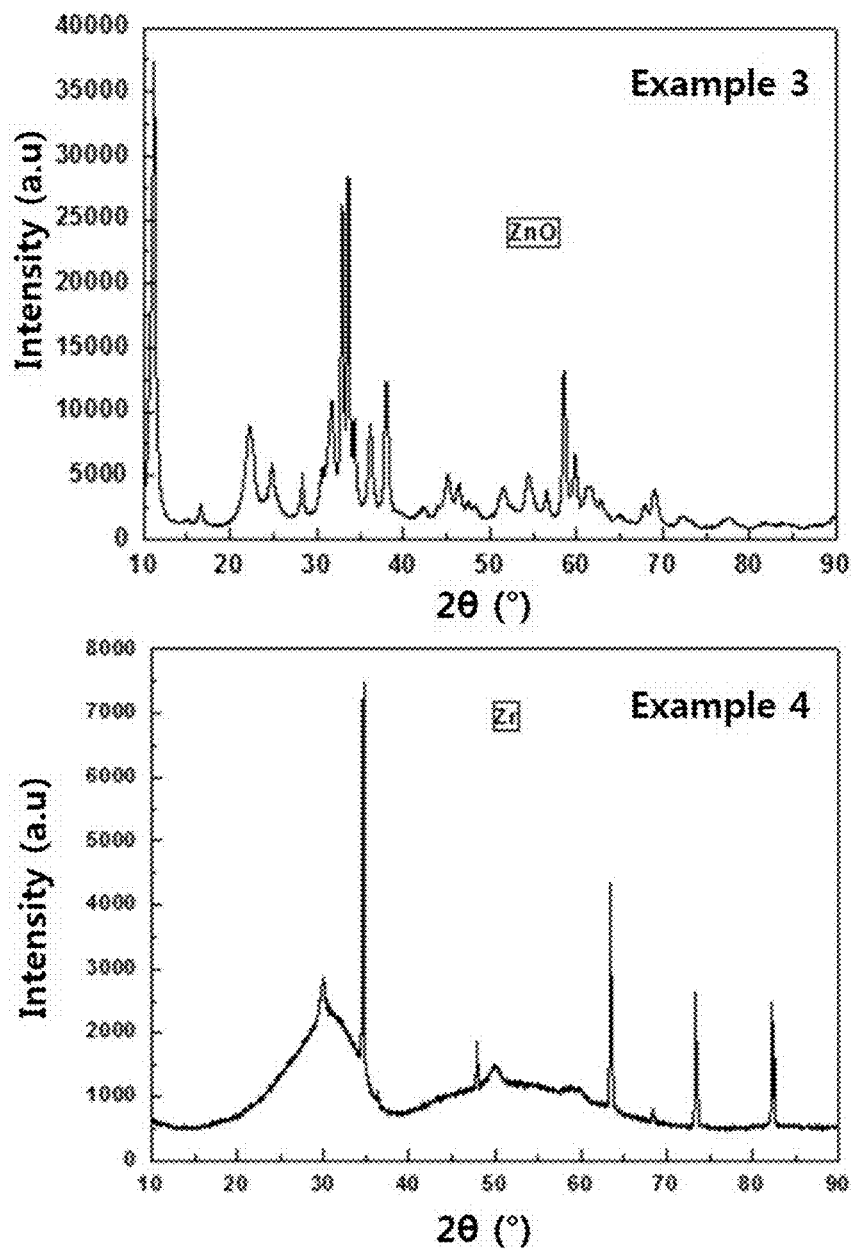

[Fig. 5]
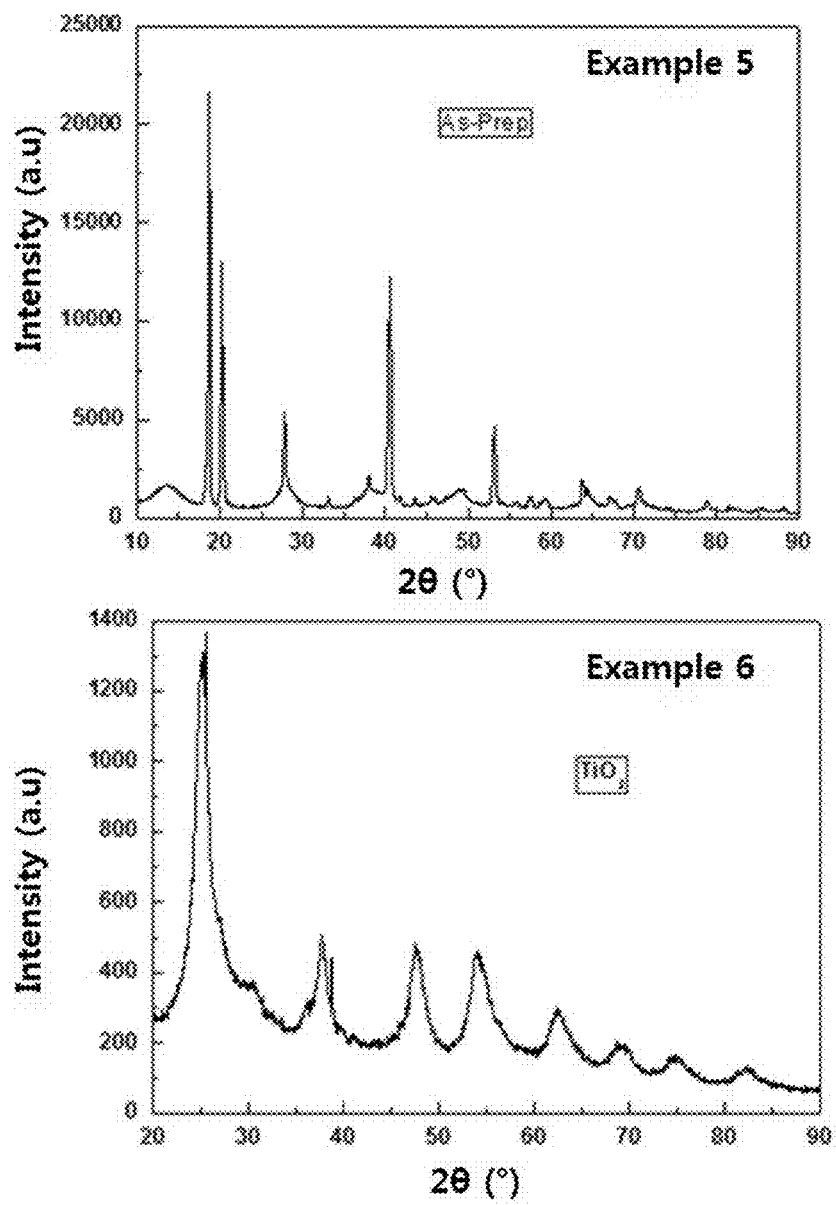

[Fig. 6]
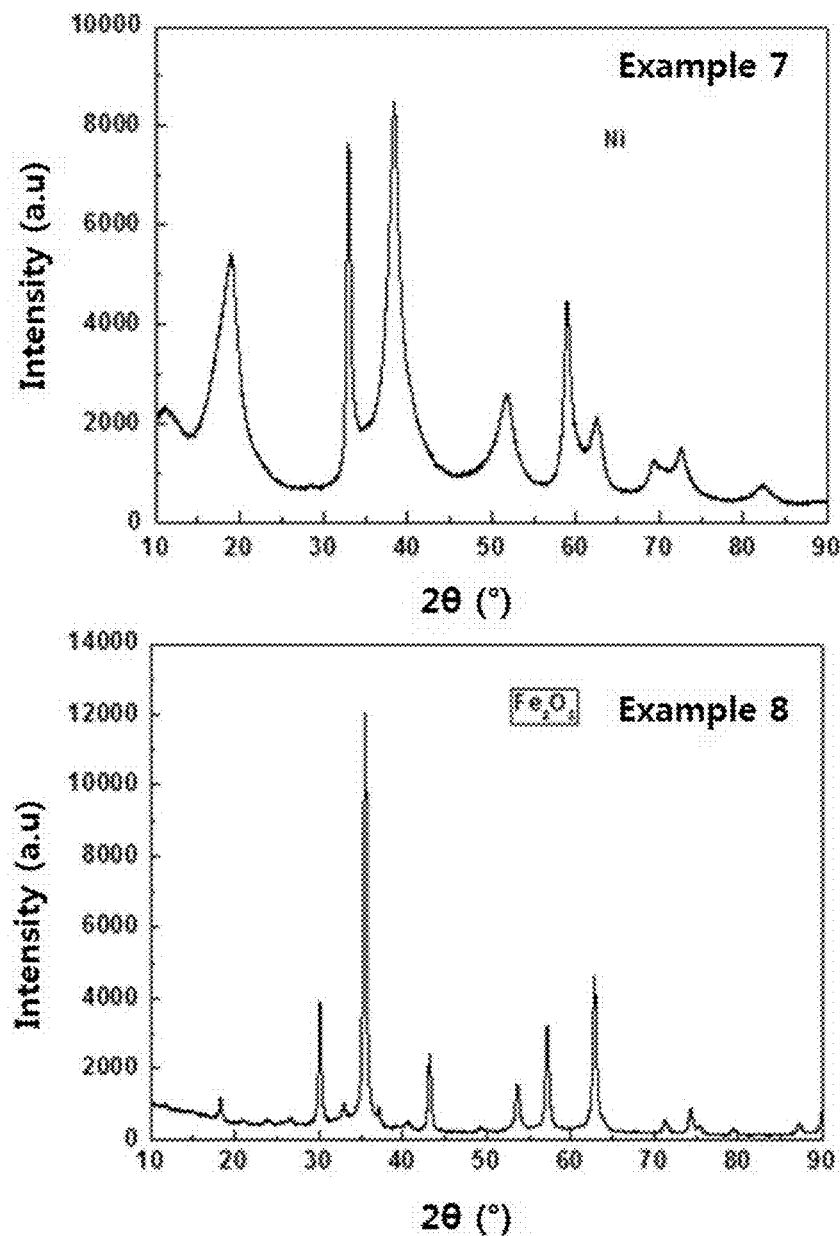

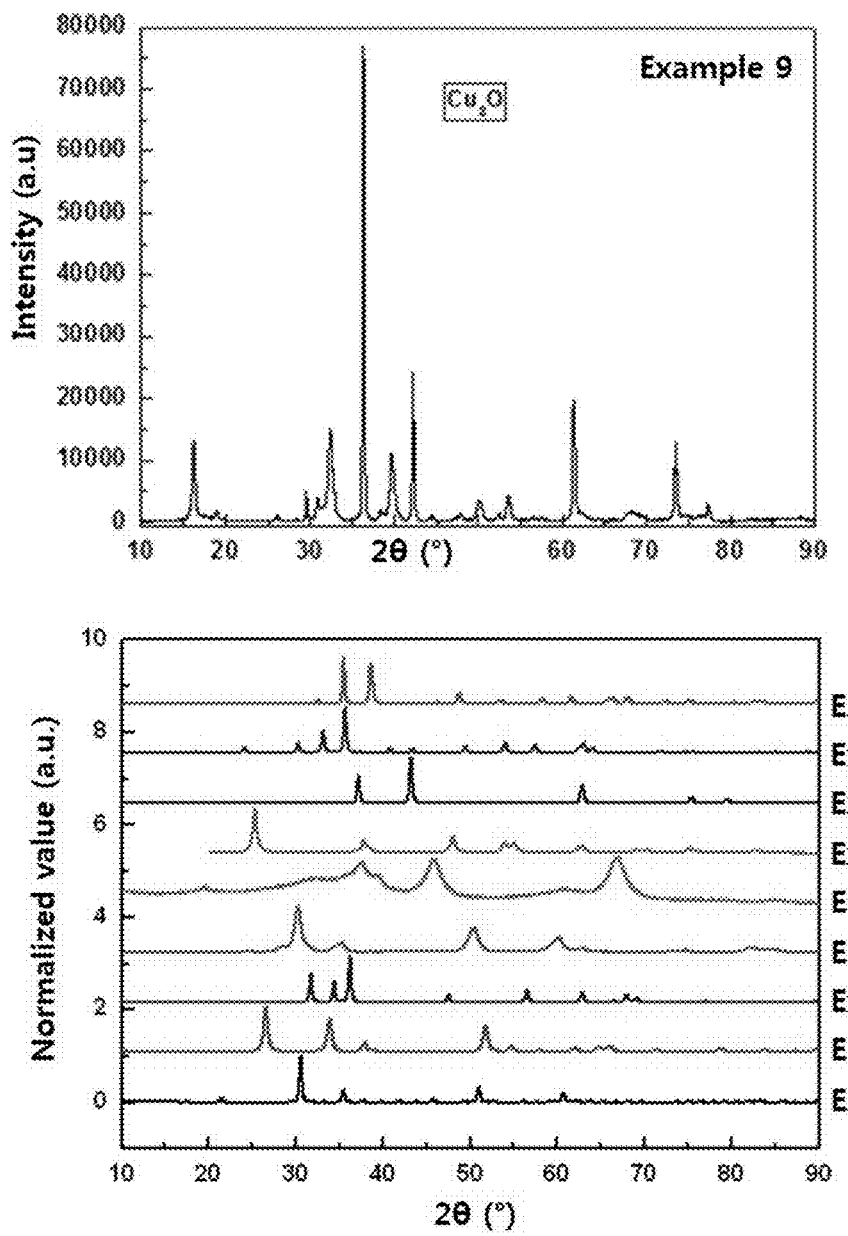
[Fig. 7]

[Fig. 8]
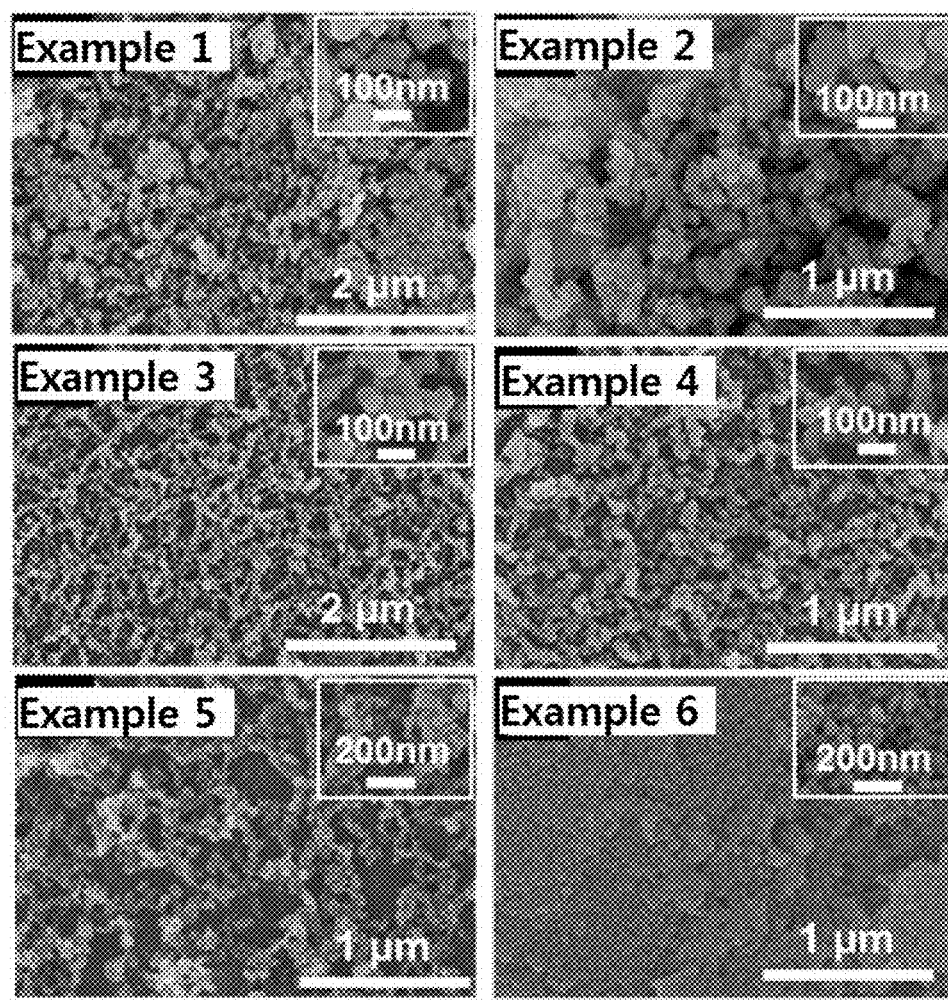

[Fig. 9]
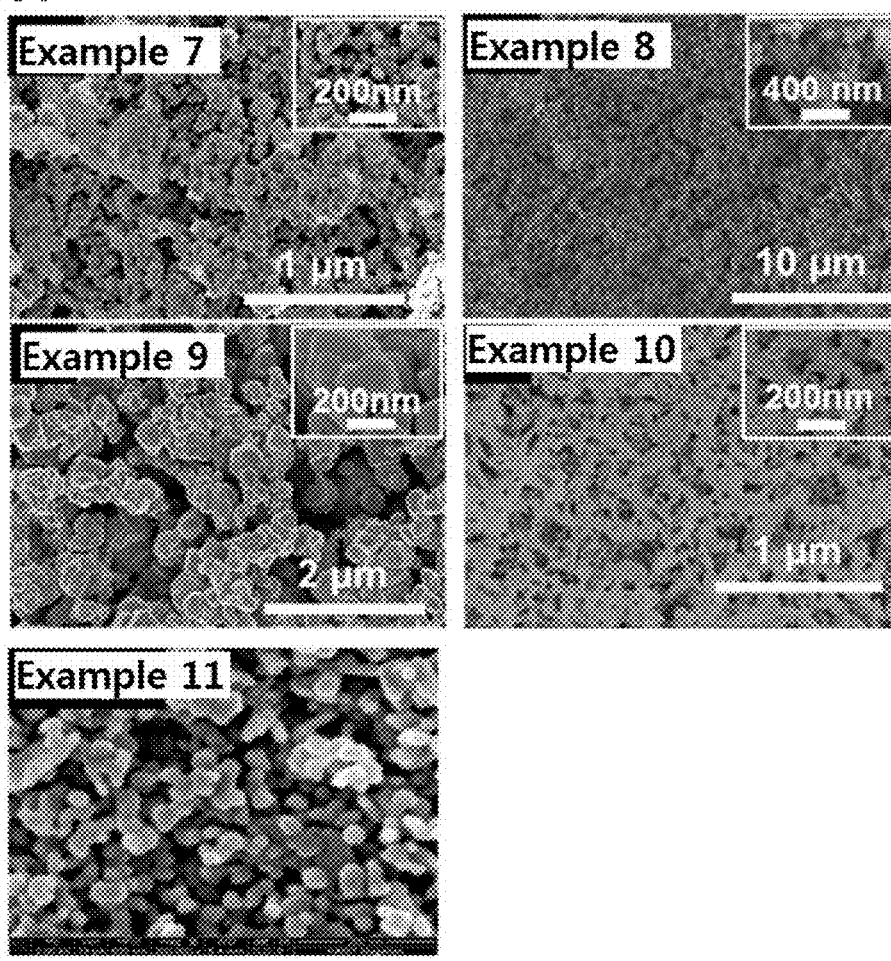

[Fig. 10]
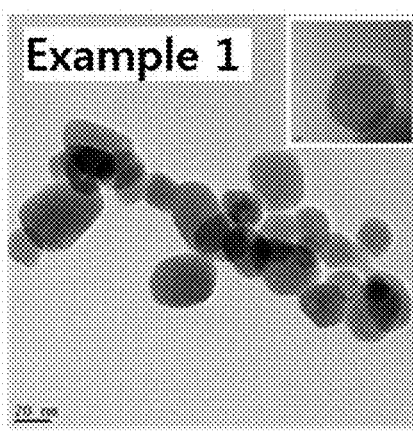
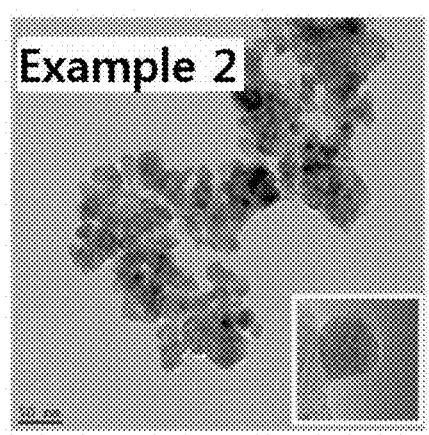
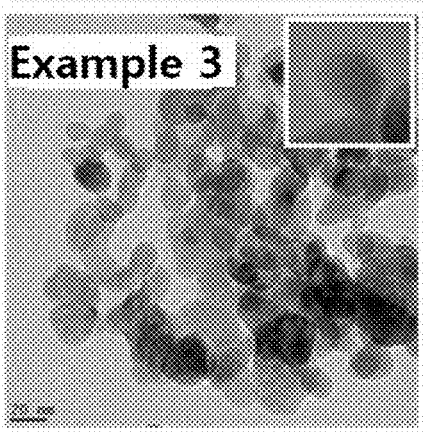
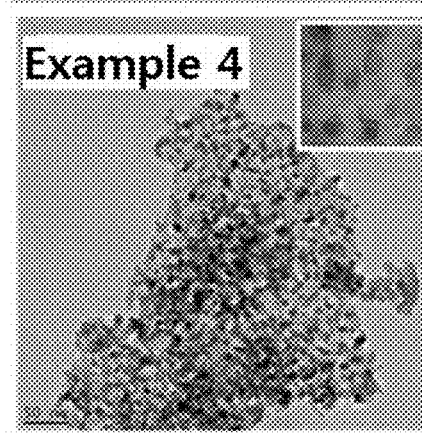
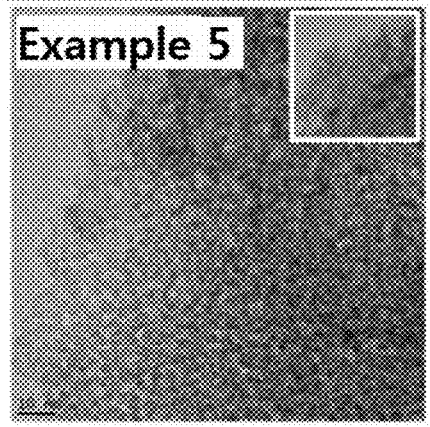
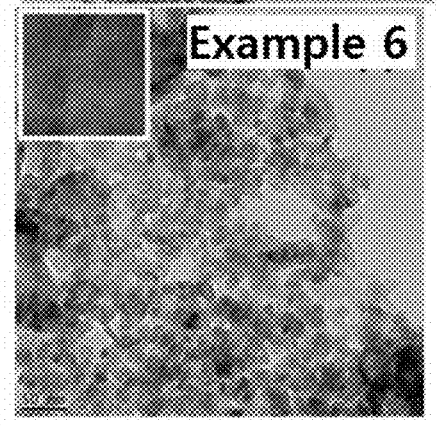

[Fig. 11]
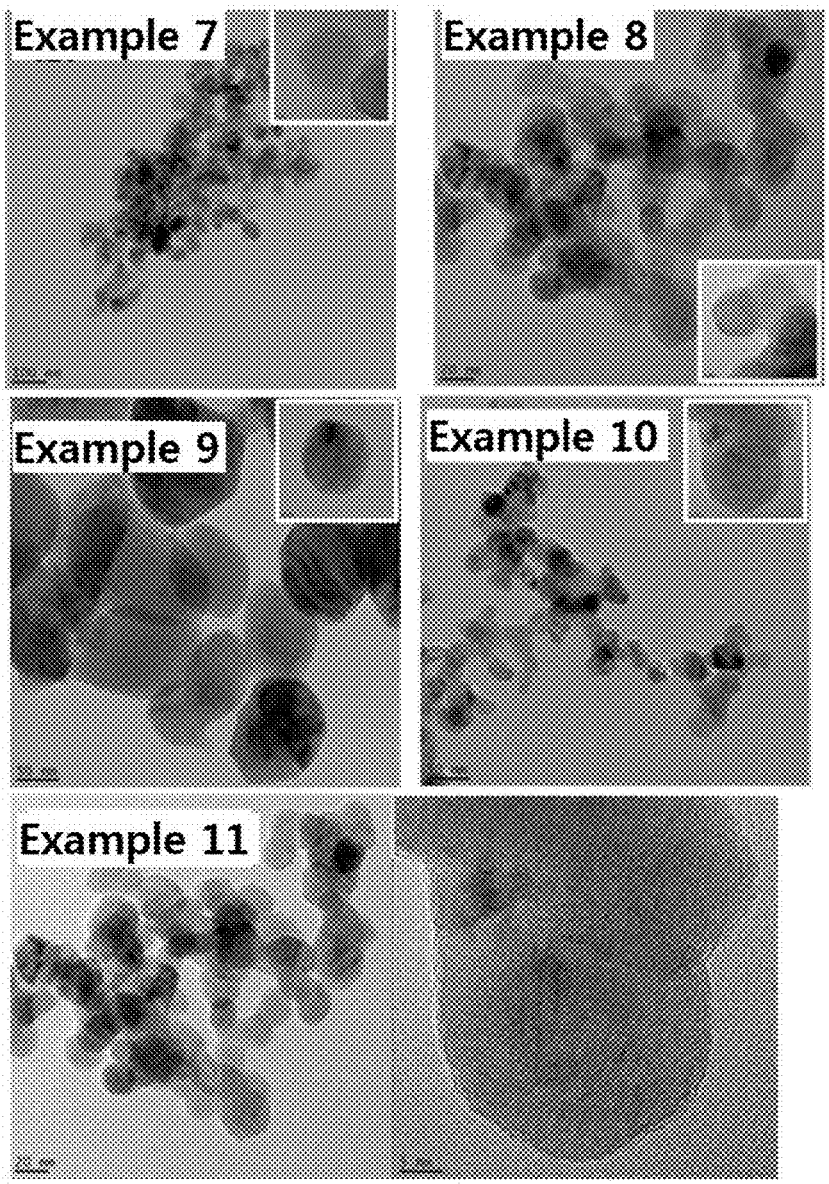

[Fig. 12]
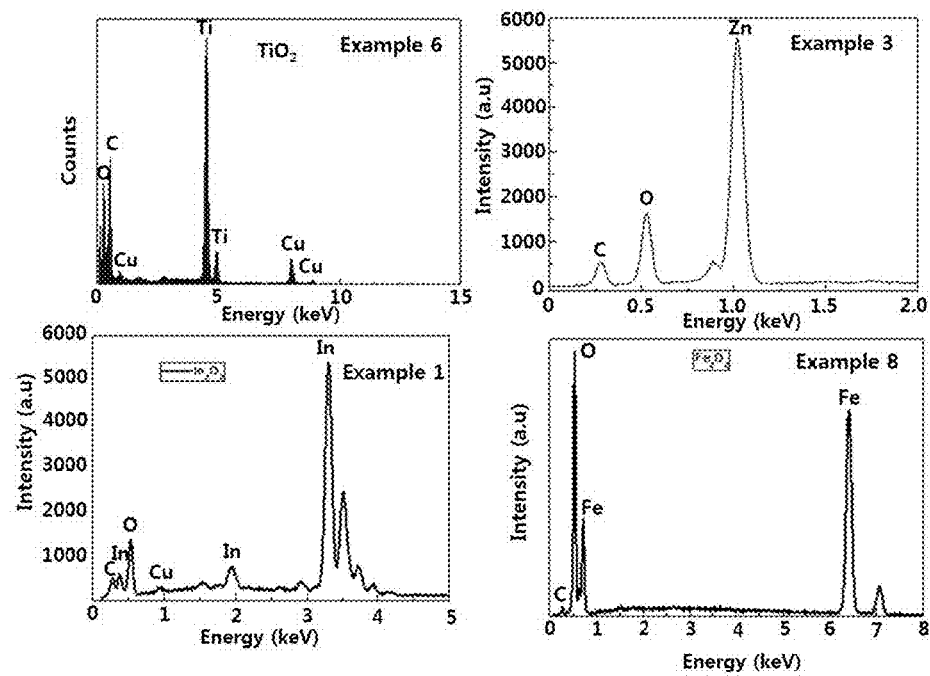

[Fig. 13]
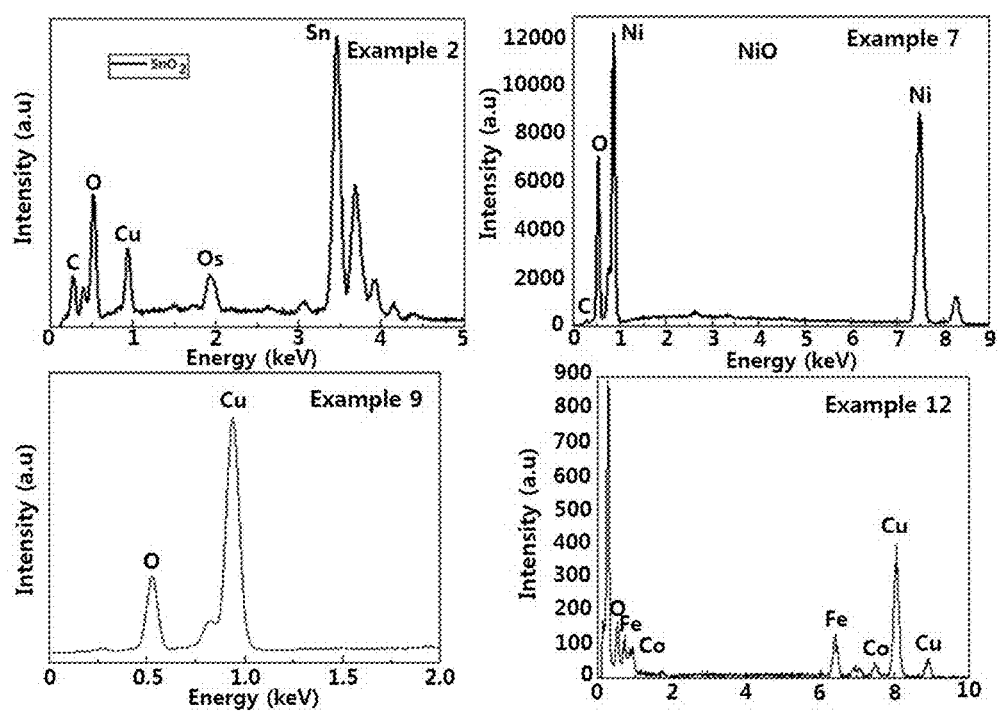

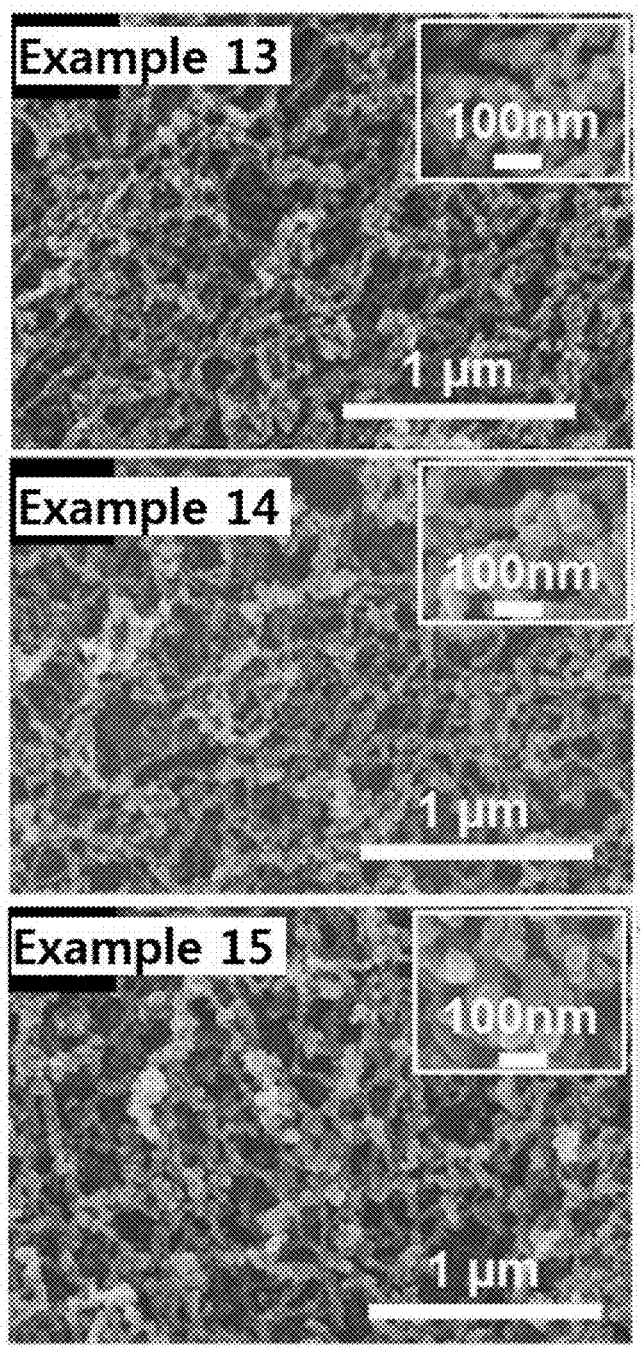
[Fig. 14]

[Fig. 15]
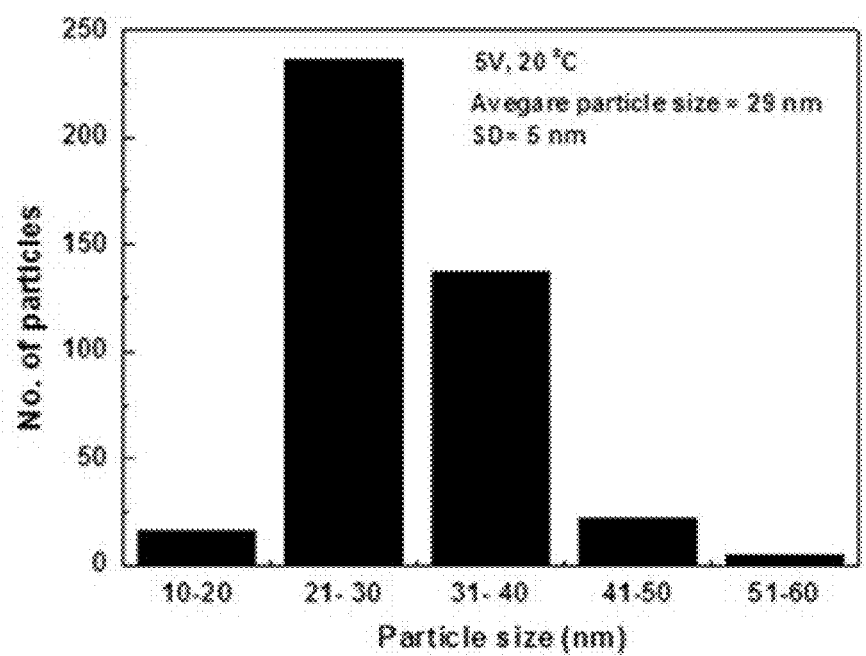

[Fig. 16]
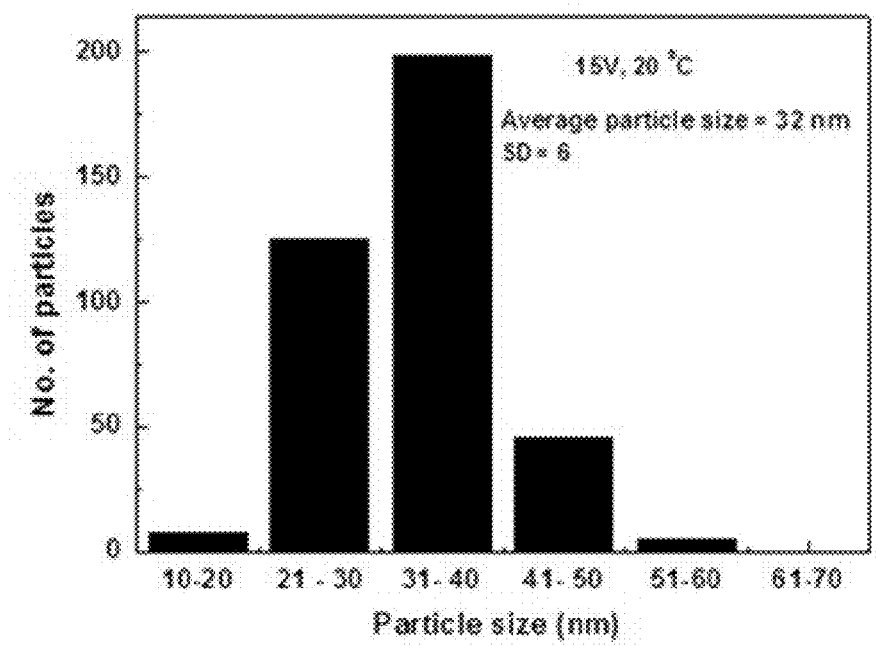

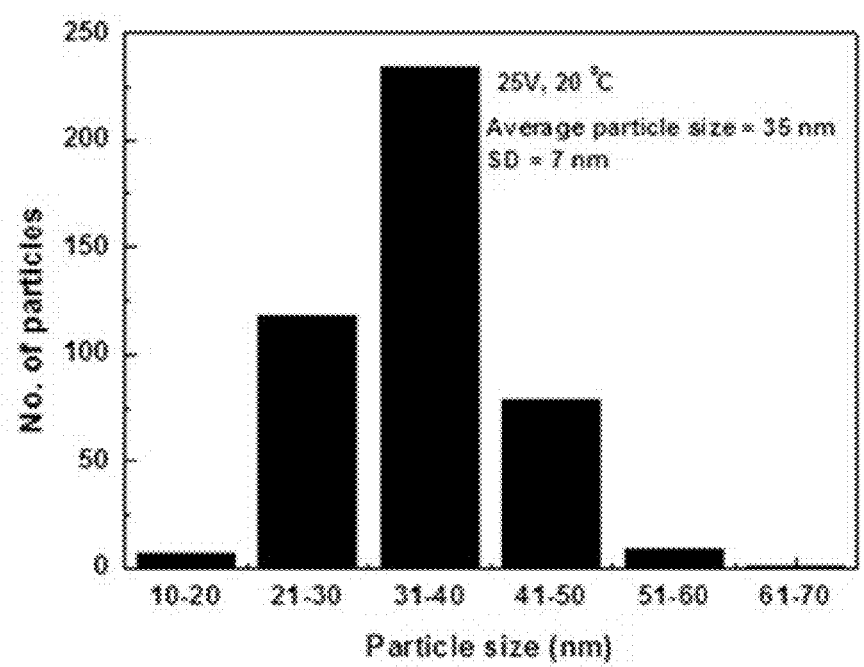
[Fig. 17]

[Fig. 18]
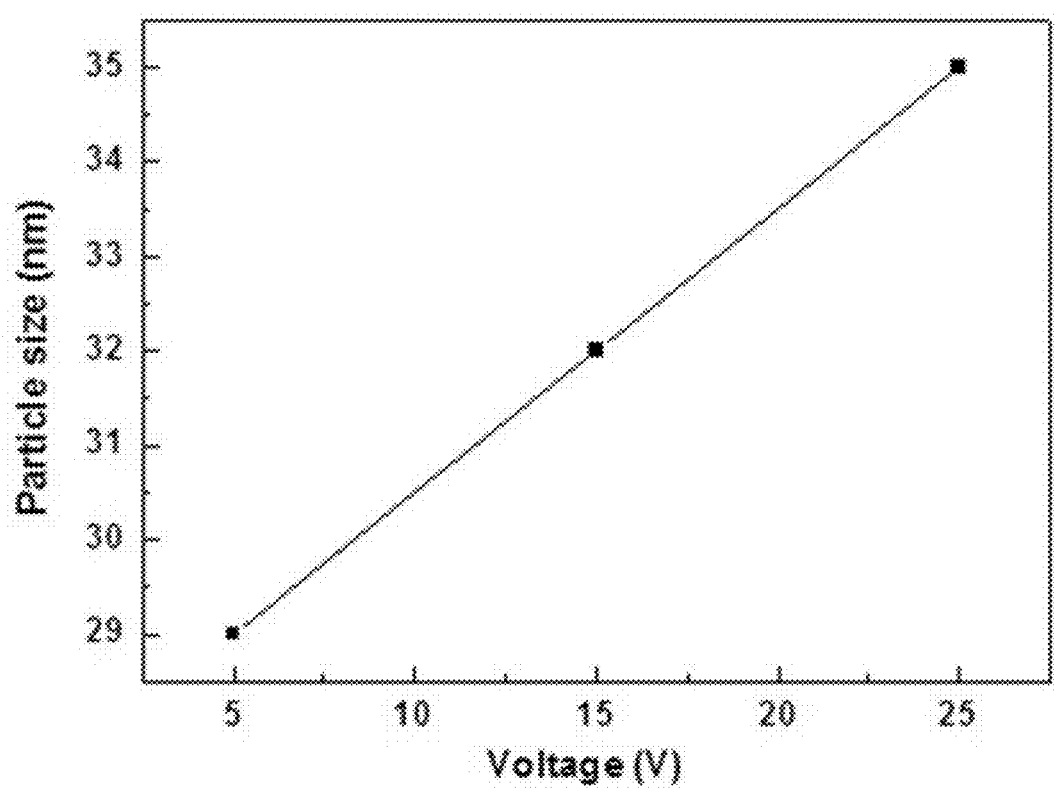

METHOD FOR MANUFACTURING OF METAL OXIDE NANOPARTICLES AND METAL OXIDE NANOPARTICLES THEREBY

CROSS-REFERENCES TO RELATED APPLICATION

This patent application claims the benefit of priority from Korean Patent Application No. 10-2014-0045884, filed on Apr. 17, 2014, the contents of which are incorporated herein by reference.

BACKGROUND OF THE INVENTION

1. Field of the Invention

The present invention relates to a method for preparing metal oxide nanoparticles and metal oxide nanoparticles prepared thereby, and more particularly, to a method for preparing metal oxide nanoparticles by dipping an anode formed of a metal forming oxide and a cathode in an electrolyte solution containing a halogen salt, and applying voltage to the anode and the cathode, and metal oxide nanoparticles prepared thereby.

2. Description of the Related Art

Among functional materials synthesized in a nano-scale, metal oxide nanoparticles are a material that is most likely to be applicable to industry. Since the metal oxide nanoparticles have physically, chemically and electrically intrinsic characteristics, the metal oxide nanoparticles may be applied to various fields.

Up to now, methods, such as a co-precipitation method, hydrolytic and non-hydrolytic sol-gel methods, a microemulsion method, a hydrothermal/solvothermal method, a microwave, a thermal decomposition, a chimie douce, a sonochemical method, and template syntheses, have been used for synthesizing the metal oxide nanoparticles.

The aforementioned typical nanoparticle synthesizing methods have inherent disadvantages and limitations. The inherent disadvantages and limitations are that an expensive precursor is required, a process is performed under high temperature and high pressure conditions, a surfactant is required (where there is a possibility of contamination due to the surfactant), a long time is taken, or a complex preparing process having a multi-stage is required. For preparing specific metal oxide, the methods may be often used in combination with each other.

Meanwhile, a typical technology related to a method for preparing metal oxide, for example, Korea Publication Patent No. 10-2004-0048093 discloses a method for preparing metal oxide nanoparticles of which a particle size distribution is mono-dispersed, and metal oxide nanoparticles prepared by the same. In more detail, Korea Publication Patent No. 10-2004-0048093 discloses a method for preparing metal oxide nanoparticles, which includes: a) adding a surfactant into a dispersed organic solvent to prepare a surfactant solution; b) mixing the surfactant solution and a metallic salt solution to prepare a first water-in-oil emulsion; c) mixing the surfactant solution and a base solution to prepare a second water-in-oil emulsion; d) mixing the first water-in-oil emulsion and the second water-in-oil emulsion to react metallic salt and the base solution and to prepare a metal oxide nanoparticle colloid solution; and e) washing, separating and drying the metal oxide nanoparticle colloid solution to obtain metal oxide nanoparticles.

However, the method has a limitation in that a surfactant is used, and a process is complicated.

Therefore, the inventors have studied a method for preparing crystalline metal oxide nanoparticles through a more simple and rapid method that does not use a surfactant, have found a method capable of preparing metal oxide by dipping an anode constituted of a metal wire or a metal sheet and a cathode, in an electrolyte containing halogen salt and applying voltage to the anode and the cathode to oxidize the anode, and eventually completed the present invention.

SUMMARY OF THE INVENTION

One object of the present invention is to provide a lithium ion battery including the metal oxide nanoparticles.

Another object of the present invention is to provide a method for adjusting a size of metal oxide nanoparticles.

In order to achieve the objects, the present invention provides a method for preparing metal oxide nanoparticles, the method including: dipping a cathode and an anode formed of a metal for forming oxide, in an inorganic electrolyte solution containing a halogen salt (step 1); and applying voltage to the anode and the cathode to form, on the anode, a metal oxide forming an anode surface (step 2).

The present invention also provides a metal oxide nanoparticle being prepared according the method and having a diameter of 1 nm to 10 nm.

Furthermore, the present invention provides a lithium ion battery including the metal oxide nanoparticle.

Furthermore, the present invention provides a method for adjusting a size of metal oxide nanoparticles, the method including: dipping a cathode and an anode formed of a metal for forming oxide, in an inorganic electrolyte solution containing halogen salt (step 1); and adjusting a voltage applied to the anode and the cathode (step 2).

According to a method for preparing metal oxide nanoparticles of the present invention, disadvantages of typical nanoparticle synthesizing methods may be solved to cheaply and rapidly manufacture nanoparticles having various structures through a simple and single process without using a surfactant.

Since an anodizing method requires only a power supply device having a low voltage of 30 V or less and an electrolyte, and is performed at room temperature, the anodizing method does not require an additional device or installation.

Also, from just after the power supply device is turned on, metal oxide nanoparticles may be rapidly formed, nanoparticles having excellent crystallinity may be produced, and factors of the anodizing method, such as voltage, temperature, an electrolyte, and an electrolyte concentration may be changed to simply adjust a shape of the nanoparticles.

Therefore, the present technology is expected to improve economical efficiency of the metal oxide nanoparticles to also contribute to the mass production of the metal oxide nanoparticles.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a schematic view showing a device used in a method for preparing metal oxide nanoparticles according to the present invention;

FIG. 2 shows a microscopy image of metal oxide nanoparticles prepared in Example 16;

FIGS. 3 to 7 are graphs showing X-ray diffraction images of metal oxide nanoparticles prepared in Examples 1 to 9;

FIGS. 8 and 9 show field-emission scanning electron microscope images of metal oxide nanoparticles prepared in Examples 1 to 11;

FIGS. 10 and 11 show transmission electron microscope images of metal oxide nanoparticles prepared in Examples 1 to 11;

FIGS. 12 and 13 are graphs showing energy-dispersive X-ray analysis images of nanoparticles prepared in Examples 1 to 3, 6 to 8, 9 and 12;

FIG. 14 shows field-emission scanning electron microscope images of metal oxide nanoparticles prepared in Examples 13 to 15;

FIGS. 15 to 17 is a graph showing a particle size distribution of metal oxide nanoparticles prepared in Examples 13 to 15; and FIG. 18 is a graph showing a size according to applied voltage of metal oxide nanoparticles prepared in Examples 13 to 15.

DESCRIPTION OF THE PREFERRED EMBODIMENTS

The present invention provides a method for preparing metal oxide nanoparticles, which includes dipping a cathode and an anode formed of a metal for forming oxide, in an inorganic electrolyte solution containing halogen salt (step 1); and applying voltage to the anode and the cathode to form, on the anode, metal oxide forming an anode surface.

In a typical method for preparing metal oxide nanoparticles, an expensive precursor is required, a process is performed under high temperature and high pressure conditions, a surfactant is required (where there is a possibility of contamination due to the surfactant), the time is consumed, or a complex preparing process having a multi-stage is required.

However, in the present invention, high temperature and high pressure conditions are not required, even though a surfactant is not used, individual particles are well separated from each other, and crystalline metal oxide nanoparticles may be prepared through a simple process and in a short time.

Hereinafter, a method for preparing metal oxide nanoparticles according to the present invention will be described in detail for each step.

In the method for preparing the metal oxide nanoparticles according to the present invention, step 1 is a step of dipping a cathode and an anode formed of a metal forming oxide, in an inorganic electrolyte solution containing a halogen salt.

At this time, a surfactant is not used, and a halogen salt-containing solution may be used as an electrolyte.

The halogen salt-containing solution is cheaper and is easier to find than organic solvents including a surfactant. Also, the surfactant is poisonous and thus is not environmentally-friendly, whereas since the halogen salt-containing solution used in the present invention uses ions (for example, $K^+$, $Na^+$ and $Cl^-$) that are abundant even in nature, the halogen salt-containing solution is eco-friendly.

Furthermore, when the surfactant is contained, nanoparticles containing a high percentage of impurities may be prepared, but since the surfactant is not used in the present invention, high purity nanoparticles may be prepared.

The metal of the step 1 may be at least one selected the group consisting of indium, tin, zinc, zirconium, aluminum, titanium, nickel, iron and copper, but is not limited thereto.

Like this, the present invention does not use a specific metal, but may use various metals and alloys as an anode to prepare various metal oxides.

The anode of the step 1 may have a wire shape or a sheet shape, but is not limited thereto, and the shape of the anode, which is able to be oxidized through electrolysis, may be appropriately selected to be used.

The cathode of the step 1 may use platinum, but is not limited thereto, and a cathode capable of oxidizing the anode may be appropriately selected to be used.

The halogen salt of the step 1 may use NaCl, KCl or a mixture thereof, but is not limited thereto.

The halogen salt is cheaper and is easier to find than the surfactant used in the typical method, and is eco-friendly.

The inorganic electrolyte solution of the step 1 may have a concentration of 0.2 M or 3.5 M.

The shape of a metal oxide to be prepared may be adjusted by adjusting the concentration of the inorganic electrolyte solution.

When the inorganic electrolyte solution of the step 1 has a concentration of less than 0.2 M, metal oxide may not be rapidly formed, and when the inorganic electrolyte solution of the step 1 has a concentration of more than 3.5 M, an electrolyte may not be dissolved in water.

In the method for preparing the metal oxide nanoparticles according to the present invention, step 2 is a step of applying voltage to the anode and the cathode to form, on the anode, metal oxide forming an anode surface.

At this time, the voltage of the step 2 may be applied in a range of 5 V to 30 V.

In the present invention, the metal oxide may be prepared even in the low voltage range, and the size of the metal oxide may be adjusted by adjusting the voltage level.

When the voltage of the step 2 is less than 5 V, the metal oxide may not be formed, and when the voltage is applied in excess of 30 V, current excessively flows to evaporate the solution, so an unexpected result may be produced in a preparing process.

The step 2 may be performed in a temperature range of 0° C. to 100° C.

In the present invention, metal oxide nanoparticles may be prepared in a temperature range of 0° C. to 100° C., or in a relatively low temperature range compared to the typical method for preparing metal oxide nanoparticles.

When the step 2 is performed at a temperature of 0° C. or less, since the solution may be frozen not to proceed a reaction, and when the step 2 is performed at a temperature of more than 100° C., the solution may be boiled.

Meanwhile, before performing the step 1, the method for preparing the metal oxide nanoparticles of the present invention may further include ultrasonic-treating, washing and drying the anode.

Since the steps are performed, a higher purity metal oxide may be formed, and the metal oxide may be more smoothly formed.

At this time, the ultrasonic-treating may be performed in at least one solvent selected from the group consisting of acetone, isopropyl, alcohol and methanol, but is not limited thereto.

Also, the ultrasonic-treating may be performed several times.

The washing may be performed by using deionized water, the drying may be performed by using high pressure air, but the washing and the drying are not limited thereto.

Also, after performing the step 2, the method for preparing the metal oxide nanoparticles of the present invention may further include firing, washing, ultrasonic-treating, centrifuging and then firing the prepared metal oxide nanoparticles.

Since the steps are further performed, the prepared metal oxide nanoparticles may be separated and collected.

At this time, the firing may be performed in a temperature range of 300+ C. to 600° C.

When the firing is performed at a temperature of less than 300° C., crystallinity may not well appear.

Also, the firing may be performed for 1 hour to 5 hours while temperature rises at a rate of 1° C./minute to 10° C./minute, but is not limited thereto.

The present invention provides metal oxide nanoparticles that are manufactured through the methods and have a diameter of 1 nm to 10 nm.

The metal oxide nanoparticles according to the present invention are well separated from each other.

Also, the metal oxide nanoparticles have crystallinity without annealing, and are prepared without using a surfactant to have a high purity. Furthermore, the size of nanoparticles to be prepared may be adjusted by adjusting the voltage level.

The present invention provides a lithium ion battery, a drug delivery material and a catalyst that include the metal oxide nanoparticles.

Since the metal oxide nanoparticles according to the present invention may be prepared through a simple process and in a short time, the metal oxide nanoparticles may be mass-produced, and be applied to all metals.

Therefore, the metal oxide nanoparticles may contribute to various fields such as a lithium ion battery, a supercapacitor, a catalyst, a gas sensor, a solar cell, an MRI, a high heat treatment and drug delivery, and an absorption and separation.

The present invention provides a method for adjusting a size of metal oxide nanoparticles, which includes dipping a cathode and an anode formed of a metal for forming oxide, in an inorganic electrolyte solution containing halogen salt (step 1); and adjusting a voltage applied to the anode and the cathode (step 2).

In the present invention, the size of metal oxide nanoparticles may be adjusted at room temperature through a simple method for adjusting voltage in electrolyzing even though a surfactant is not used.

Hereinafter, a method for adjusting a size of metal oxide nanoparticles according to the present invention will be described in detail for each step.

In the method for adjusting the size of the metal oxide nanoparticles, step 1 is a step of dipping a cathode and an anode formed of a metal for forming oxide, in an inorganic electrolyte solution containing a halogen salt.

At this time, even though a surfactant is not used, a halogen salt-containing solution may be used as an electrolyte.

The metal of the step 1 may be at least one selected the group consisting of indium, tin, zinc, zirconium, aluminum, titanium, nickel, iron and copper, but is not limited thereto.

The anode of the step 1 may have a wire shape or a sheet shape, but is not limited thereto, a shape of an anode that is able to be oxidized through electrolysis, may be appropriately selected to be used.

The cathode of the step 1 may use platinum, but is not limited thereto, a cathode capable of oxidizing the anode, may be appropriately selected to be used.

The halogen salt of the step 1 may use NaCl, KCl or a mixture thereof, but is not limited thereto.

The inorganic electrolyte solution of the step 1 may have a concentration of 0.2 M or 3.5 M.

When the inorganic electrolyte solution of the step 1 has a concentration of less than 0.2 M, metal oxide may not be rapidly formed, and when the inorganic electrolyte solution of the step 1 has a concentration of more than 3.5 M, an electrolyte may not be dissolved in water.

In the method for adjusting the size of the metal oxide nanoparticles according to the present invention, the step 2 is a step of adjusting a voltage applied to the anode and the cathode.

As voltage is increased, large-sized metal oxide nanoparticles may be prepared, and as voltage is decreased, small-sized metal oxide nanoparticles may be prepared.

At this time, the voltage of the step 2 may be applied in a range of 5 V to 30 V.

When the voltage of the step 2 is of less than 5 V, metal oxide may not be formed, and when the voltage is applied in excess of 30 V, current excessively flows to evaporate the solution, so an irregular result may be produced in a preparing process.

The step 2 may be performed in a temperature range of 0° C. to 100° C.

When the step 2 is performed at a temperature of 0° C. or less, since the solution may be frozen not to proceed a reaction, and when the step 2 is performed at a temperature of more than 100° C., the solution may be boiled.

Meanwhile, before performing the step 1, the method for preparing the metal oxide nanoparticles of the present invention may further include ultrasonic-treating, washing and drying the anode.

At this time, the ultrasonic-treating step may be performed in at least solvent selected from the group consisting of acetone, isopropyl, alcohol and methanol, but is not limited thereto.

Also, the ultrasonic-treating step may be performed several times.

The washing may be performed by using deionized water, the drying may be performed by using high pressure air, but the washing and the drying are not limited thereto.

Further, after performing the step 2, the method for preparing the metal oxide nanoparticles of the present invention may further include firing, washing, ultrasonic-treating, centrifuging and then firing the prepared metal oxide nanoparticles.

Since the steps arte performed, the prepared metal oxide nanoparticles may be separated and collected.

At this time, the firing may be performed in a temperature range of 300° C. to 600° C.

When the firing is performed at a temperature of less than 300° C., crystallinity may not well appear.

Hereinafter, the present invention will be described in more detail though Examples. However, the following embodiments are strictly for the purpose of explaining the present invention, and do not limit the scope of the present invention.

<Example 1> Preparing of Indium Oxide ($In_2O_3$) Nanoparticles

Step 1: An indium metal wire (having a purity of 99.9% and purchased from Nilaco Corporation) was ultrasonic-treated in acetone, isopropyl, alcohol and methanol for 5 minutes, respectively, was washed by deionized water, and was dried by using high pressure air to be prepared as an anode. Platinum having a size of 15×25×0.2 $mm^3$ was prepared as a cathode.

A solution made by dissolving potassium chloride (purchased from Sigma Aldrich) in deionized water was prepared in a concentration of 1M as an electrolyte.

The anode and the cathode were dipped in the electrolyte.

Step 2: A voltage of 10 V was applied to the anode and the cathode of Step 1 to prepare a metal oxide while the electrolyte was maintained at a temperature of 20° C.

The generated various metal oxide nanoparticles were washed enough to wash out a salt by using deionized water, were ultrasonic-treated and then were collected by using a centrifugal separator. After that, the collected nanoparticles were fired by elevating the temperature at a rate of 3° C. per minute from a temperature of 450° C., and were cooled at room temperature to prepare indium oxide nanoparticles.

<Example 2> Preparing of Tin Oxide ($SnO_2$) Nanoparticles

Except that a tin metal wire was used as an anode unlike in the Step 1 of Example 1, Example 2 was performed in the same manner as Example 1 to prepare tin oxide nanoparticles.

<Example 3> Preparing of Zinc Oxide (ZnO) Nanoparticles

Except that a zinc metal wire was used as an anode unlike in the Step 1 of Example 1, Example 3 was performed in the same manner as Example 1 to prepare zinc oxide nanoparticles.

<Example 4> Preparing of Zirconium Oxide ($ZrO_2$) Nanoparticles

Except that a zirconium metal wire was used as an anode unlike in the Step 1 of Example 1, Example 4 was performed in the same manner as Example 1 to prepare zirconium oxide nanoparticles.

<Example 5> Preparing of Aluminum Oxide ($Al_2O_3$) Nanoparticles

Except that an aluminum metal wire was used as an anode unlike in the Step 1 of Example 1, Example 5 was performed in the same manner as Example 1 to prepare aluminum oxide nanoparticles.

<Example 6> Preparing of Titanium Oxide ($TiO_2$) Nanoparticles

Except that a titanium metal wire was used as an anode unlike in the Step 1 of Example 1, Example 6 was performed in the same manner as Example 1 to prepare titanium oxide nanoparticles.

<Example 7> Preparing of Nickel Oxide (NiO) Nanoparticles

Except that a nickel metal wire was used as an anode unlike in the Step 1 of Example 1, Example 7 was performed in the same manner as Example 1 to prepare nickel oxide nanoparticles.

<Example 8> Preparing of Iron Oxide ($Fe_2O_3$) Nanoparticles

Except that an iron metal wire was used as an anode unlike in the Step 1 of Example 1, Example 8 was performed in the same manner as Example 1 to prepare iron oxide nanoparticles.

<Example 9> Preparing of Copper Oxide (CuO) Nanoparticles

Except that a copper metal wire was used as an anode unlike in the Step 1 of Example 1, Example 9 was performed in the same manner as Example 1 to prepare copper oxide nanoparticles.

<Example 10> Preparing of Nickel Ferrite ($NiFe_2O_4$) Nanoparticles

Except that a nickel-iron alloy wire (where a nickel content is 50 weight %, and an iron content is 50 weight %) was used as an anode unlike in the Step 1 of Example 1, Example 10 was performed in the same manner as Example 1 to prepare nickel ferrite nanoparticles.

<Example 11> Preparing of Cobalt Ferrite ($CoFe_2O_4$) Nanoparticles

Except that a cobalt-iron alloy wire (where a cobalt content is 50 weight %, and an iron content is 50 weight %) was used as an anode unlike in the Step 1 of Example 1, Example 11 was performed in the same manner as Example 1 to prepare cobalt ferrite nanoparticles.

<Example 12> Preparing of Copper-Cobalt Ferrite ($Cu_1CO_1Fe_2O_5$) Nanoparticles Except that a copper-cobalt-iron alloy wire (where a copper content is 33.3 weight %, a cobalt content is 33.3 weight %, and an iron content is 33.3 weight %) was used as an anode unlike in the Step 1 of Example 1, Example 12 was performed in the same manner as Example 1 to prepare copper-cobalt ferrite nanoparticles.

<Example 13> Preparing of Indium Oxide ($In_2O_3$) Nanoparticles (5V)

Except that a voltage of 5 V was applied unlike in the Step 2 of Example 1, Example 13 was performed in the same manner as Example 1 to prepare indium oxide nanoparticles.

<Example 14> Preparing of Indium Oxide ($In_2O_3$) Nanoparticles (15 V)

Except that a voltage of 15 V was applied unlike in the Step 2 of Example 1, Example 14 was performed in the same manner as Example 1 to prepare indium oxide nanoparticles.

<Example 15> Preparing of Indium Oxide ($In_2O_3$) Nanoparticles (25 V)

Except that a voltage of 25 V was applied unlike in the Step 2 of Example 1, Example 15 was performed in the same manner as Example 1 to prepare indium oxide nanoparticles.

Example 16

Except that nanoparticles were collected by using a centrifugal separator, and then were dried in an oven having a temperature of 60° C. for 12 hours unlike in the Step 2 of Example 3, Example 16 was performed in the same manner as Example 3 to prepare zinc oxide nanoparticles.

Example 17

Except that sodium chloride was used as an electrolyte instead of potassium chloride unlike in the Step 1 of Example 1, Example 17 was performed in the same manner as Example 1 to prepare zinc oxide nanoparticles.

<Experimental Example 1> Observing the Preparation of a Metal Oxide

In order to confirm the preparation of the metal oxide of Example 16, metal oxide nanoparticles were observed with the naked eye, and the observed result was shown in FIG. 2.

As shown in FIG. 2, it may be confirmed that white zinc oxide is formed through an anodizing method to be precipitated, and it may seen that when the white zinc oxide is centrifuged and then is dried, white nanoparticles are obtained in a large amount.

<Experimental Example 1> Observing Crystallinity of Metal Oxide

In order to confirm crystallinity of metal oxides prepared in Examples 1 to 9, metal oxide nanoparticles were observed with an X-ray diffraction analyzer, and the observed results were shown in FIGS. 3 to 7.

As shown in FIGS. 3 to 7, it may be seen that each of metal oxides shows a specific peak.

Accordingly, it may be seen that metal oxide prepared according to the present invention shows crystallinity, and also has a high purity. The crystallinity of nanoparticles described above is caused due to an high temperature electrolyte that is raised to a temperature of 90° C. during anodizing. Also, since a surfactant is not used, it may be seen that the nanoparticles have high purity.

<Experimental Example 1> Observing a Structure of Metal Oxide

In order to confirm a micro structure of metal oxides prepared in Examples 1 to 11, after metal oxide nanoparticles were observed with a field-emission scanning electron microscope (FE-SEM), the observed results were shown in FIGS. 8 to 9, and after the metal oxide nanoparticles were observed with a transmission electron microscope (TEM), the observed results were shown in FIGS. 10 to 11.

As shown in FIGS. 8 to 9, it may be seen that particles of each metal oxides haves a globular shape, and exist in a well separate state from each other. Also, it may be seen that each of nanoparticles is clearly observed, and lumps of nanoparticles are compressed.

As shown in FIGS. 10 and 11, it may be seen that almost all nanoparticles have a globular shape and have an average diameter of less than 10 nm. In addition, nanoparticles are uniformly distributed, and each of nanoparticles is clearly observed in a microscope image.

A size distribution may be calculated from a transmission electron microscope image and an XRD pattern, the calculated size was ±3 nm.

<Experimental Example 4> Observing a Composition of Metal Oxide

In order to analyze a component of metal oxides prepared in Example 1 to 3, 6 to 8, 9 and 12, the metal oxide particles were observed with an energy dispersive X-ray analyzer (EDAX), and the results are shown FIGS. 12 and 13.

As shown in FIGS. 12 and 13, it may be conformed that metal oxide is prepared as intended. Therefore, it may be seen that various metal oxide nanoparticles are formed through an anodizing method.

<Experimental Example 4> Observing a Size of Metal Oxide According to Voltage

In order to observe a size of metal oxides prepared in Examples 13 to 14, after metal oxide nanoparticles were observed with a field-emission scanning electron microscope (FE-SEM), the observed results were shown in FIG. 14, after the metal oxide nanoparticles were observed with using a scale of a photograph, the observed results were shown in FIGS. 15 to 17, and a size according to voltage level was shown in FIG. 18.

As shown in FIGS. 14 and 18, in a case of Example 13 in which voltage is 15 V, an average particle size was 29 nm, but as voltage was increased to 15 V and 25 V, an average particle size was increased to 32 nm and 35 nm.

Also, as a voltage was increased, a radius SD of particles was increased from 5 nm to 7 nm.

Therefore, it may seen that while voltage is adjusted in a range of 5 V to 15 V, a particle size may be adjusted in a range of 29 nm to 35 nm, and a size of particles required for a specific use may be obtained through a voltage adjustment in preparing nanoparticles.

What is claimed is:

1. A method for preparing metal oxide nanoparticles, the method comprising:
   dipping a cathode and an anode, each of the cathode and the anode being a different metal, in an inorganic electrolyte solution containing a halogen salt (step 1); and
   applying a DC voltage between the anode and the cathode so as to oxidize the metal of the anode, to form, on the anode, a metal oxide forming an anode surface (step 2), whereby the metal oxide formed is an oxide of the metal of the anode,
   wherein the anode is formed of at least one selected from the group consisting of indium, tin, zinc, zirconium, aluminum, titanium, nickel, iron and copper, and
   wherein the cathode is formed of platinum.

2. The method of claim 1, wherein a surfactant is not used.

3. The method of claim 1, wherein the anode of step 1 has a wire shape or a sheet shape.

4. The method of claim 1, wherein the halogen salt of the step 1 is NaCl, KCl or a mixture thereof.

5. The method of claim 1, wherein the inorganic electrolyte solution of step 1 has a concentration of 0.2 M to 3.5 M.

6. The method of claim 1, wherein the voltage of the step 2 is applied in a range of 5 V to 30 V.

7. The method of claim 1, wherein the step 2 is performed in a temperature range of 0° C. to 100° C.

8. The method of claim 1, further comprising ultrasonic-treating, washing and drying the anode prior to performing the step 1.

9. The method of claim 8, wherein the ultrasonic-treating is performed in at least one solvent selected from the group consisting of acetone, isopropyl, alcohol and methanol.

10. The method of claim 1, further comprising washing, ultrasonic-treating, centrifuging, and firing the prepared metal oxide particles after performing the step 2.

11. The method of claim 10, wherein the firing is performed in a temperature range of 300° C. to 600° C.

12. The method of claim 1, further comprising adjusting the DC voltage applied to the anode and the cathode to adjust the size of the metal oxide nanoparticles deposited on the anode.

* * * * *